US010286016B2

(12) United States Patent
Kim et al.

(10) Patent No.: US 10,286,016 B2
(45) Date of Patent: May 14, 2019

(54) COMPOSITIONS AND METHODS FOR TREATING GONORRHEA

(71) Applicants: ARIZONA BOARD OF REGENTS ON BEHALF OF THE UNIVERSITY OF ARIZONA, Tucson, AZ (US); THE HENRY M. JACKSON FOUNDATION FOR THE ADVANCEMENT OF MILITARY MEDICINE, INC., Bethesda, MD (US)

(72) Inventors: Won Jong Kim, Tucson, AZ (US); Maria Auxilio Rendón-Espinosa, Tucson, AZ (US); Magdalene Yh So, Tucson, AZ (US); Maira Goytia, Atlanta, GA (US); Ann Jerse, Bethesda, MD (US); Dustin Higashi, Notre Daem, IN (US)

(73) Assignees: ARIZONA BOARD OF REGENTS ON BEHALF OF THE UNIVERSITY OF ARIZONA, Tucson, AZ (US); THE HENRY M. JACKSON FOUDATION FOR THE ADVANCEMENT OF MILITARY MEDICINE, INC., Bethesda, MD (US)

(*) Notice: Subject to any disclaimer, the term of this patent is extended or adjusted under 35 U.S.C. 154(b) by 0 days.

(21) Appl. No.: 15/508,409

(22) PCT Filed: Sep. 2, 2015

(86) PCT No.: PCT/US2015/048114
§ 371 (c)(1),
(2) Date: Mar. 2, 2017

(87) PCT Pub. No.: WO2016/036839
PCT Pub. Date: Mar. 10, 2016

(65) Prior Publication Data
US 2017/0304372 A1  Oct. 26, 2017

Related U.S. Application Data

(60) Provisional application No. 62/044,776, filed on Sep. 2, 2014.

(51) Int. Cl.
*A61K 35/74* (2015.01)
*C07K 14/22* (2006.01)
*C12N 1/20* (2006.01)
*A01N 63/02* (2006.01)
*A61K 38/00* (2006.01)
*A61K 45/06* (2006.01)

(52) U.S. Cl.
CPC ............... *A61K 35/74* (2013.01); *A01N 63/02* (2013.01); *A61K 45/06* (2013.01); *C07K 14/22* (2013.01); *C12N 1/20* (2013.01)

(58) Field of Classification Search
CPC .............. C12Q 1/689; C12Q 2600/16; C12Q 2600/156; C12Q 1/14; C12Q 2600/166; C12Q 1/6893; C12Q 1/6895; C12Q 1/10; C12Q 1/6837; C12Q 2600/106; C12Q 2600/112; C12Q 2600/158; A61K 39/00; A61K 39/095; A61K 2039/55505; A61K 38/00; A61K 2039/55594; A61K 35/74; A61K 45/06; C07K 14/22; G01N 2333/195; G01N 2333/31; G01N 2800/06; G01N 33/48792; Y10S 530/806; Y10S 530/825; A61B 2503/40; A61B 5/0022; A61B 5/01; A61B 5/0205; A61B 5/024; A61B 5/02438; A61B 5/076; A61B 5/0816; A61B 5/11; A61B 5/14532; A61B 5/14542; A61B 5/682; A61J 17/003; A61J 17/006; C40B 30/02; G06F 19/24; G06F 19/28; G06F 19/3418; G06F 19/3481; G16H 50/20; Y02A 90/26; A01N 63/02; C12N 1/20
See application file for complete search history.

(56) References Cited

U.S. PATENT DOCUMENTS

| 2003/0026809 A1 | 2/2003 | Robinson et al. |
| 2009/0318382 A1 | 12/2009 | Ghigo et al. |
| 2011/0256232 A1 | 10/2011 | Nygaard et al. |

FOREIGN PATENT DOCUMENTS

| WO | 2003/006672 | 1/2003 |
| WO | 2006/036406 | 4/2006 |
| WO | 2011/077143 | 6/2011 |
| WO | 2014/078656 | 5/2014 |
| WO | 2014/121301 | 8/2014 |

OTHER PUBLICATIONS

Andrade et al. Mem. Inst. Oswaldo Cruz, Rio de Janeiro 81: 453-458, 1986.*
Higashi et al. PLoS ONE 6: e21373: 1-7, Jun. 2011.*
So M. Tribal Warfare: Killing of pathogen N. gonorrhoeae by commensal N. elongata. Research Project, Grantome, 2015: https://www.grantome.com/grant/NIH/R21-AI111944-02.*
Aagaard, K., et al., "A Metagenomic Approach to Characterization of the Vaginal Microbiome Signature in Pregnancy" PLoS One, 2012. 7(6): p. e36466.
Berry, J.L., et al., "Functional Analysis of the Interdependence between DNA Uptake Sequence and Its Cognate ComP Receptor during Natural Transformation in *Neisseria* Species" PLoS Genet, 2013. 9(12): p. e1004014.
Cartwright, K.A., et al., "The Stonehouse survey: nasopharyngeal carriage of meningococci and Neisseria lactamica." Epidemiol Infect, 1987. 99(3): p. 591-601.

(Continued)

*Primary Examiner* — Sarvamangala Devi
(74) *Attorney, Agent, or Firm* — Casimir Jones, S.C.

(57) ABSTRACT

The present invention relates to compositions and methods for preventing and/or treating gonorrhea. In particular, the present invention provides compositions comprising an effective amount of a commensal species of *Neisseria* (e.g., an effective amount of an extract of a commensal species of *Neisseria*), wherein such compositions are capable of inhibiting the growth of *Neisseria gonorrhoeae*.

3 Claims, 8 Drawing Sheets

(56) References Cited

OTHER PUBLICATIONS

Cascales, E., et al., "Colicin biology." Microbiol Mol Biol Rev, 2007. 71(1): p. 158-229.
Cole et al. "Opacity proteins increase Neisseria gonorrhoeae fitness in the female genital tract due to a factor under ovarian control." Infect Immun, 2010. 78(4): p. 1629-41.
Dillard, J.P. "Genetic Manipulation of Neisseria gonorrhoeae." Curr Protoc in Microbiol, 2011(Chapter 4:Unit4A.2), 24 pages.
Gerbase, A., et al., "Global burden of Sexually Transmitted Diseases (excluding HIV) in the year 2000" Sex Transm Dis, 2000. 15, pp. 1-27.
Hancock, V., M. Dahl, and P. Klemm, "Probiotic *Escherichia coli* strain Nissle 1917 outcompetes intestinal pathogens during biofilm formation." J Med Microbiol, 2010. 59(Pt 4): p. 392-9.
Han, X.Y., T. Hong, and E. Falsen, J "*Neisseria bacilliformis* sp. nov. isolated from human infections." Clin Microbiol, 2006. 44(2): p. 474-9.
Hobbs, M.M., et al., "Experimental Gonococcal Infection in Male Volunteers: Cumulative Experience with Neisseria gonorrhoeae Strains FA1090 and MS11mkC" Front Microbiol, 2011. 2:123; p. 1-12.
Howie, H.L., S.L. Shiflett, and M. So, "Extracellular signal-regulated kinase activation by Neisseria gonorrhoeae downregulates epithelial cell proapoptotic proteins Bad and Bim. Infection and immunity." Infect Immun, 2008. 76(6): p. 2715-21.
International Search Report and Written Opinion, International Patent Application No. PCT/US2015/048114, dated Dec. 4, 2015.
Iwase, T., et al., "*Staphylococcus epidermidis* Esp inhibits *Staphylococcus aureus* biofilm formation and nasal mlonization." Nature, 2010.465(7296): p. 346-9.
Jerse, A.E., et al., "Estradiol-Treated Female Mice as Surrogate Hosts for Neisseria gonorrhoeae Genital Tract Infections." Front Microbiol, 2011. 2:107; pp. 1-13.
Johnson-Henry, K.C., et al., "Amelioration of the Effects of Citrobacter rodentium Infection in Mice by Pretreatment with Probiotics" J Infect Dis, 2005. 191(12): p. 2106-17.
Knapp, J.S.. et al, "Prevalence and persistence of *Neisseria cinerea* and other *Neisseria* spp. in adults. J Clin Microbiol." J Clin Microbiol, 1988.26(5): p. 896-900.
Krediet, C.J., et al., "Members of native coral microbiata inhibit glycosidases and thwart colonization of coral mucus by an opportunistic pathogen." ISME J, 2013. 7(5): p. 980-90.
Laga, M., et al., "Non-ulcerative sexually transmitted diseases as risk factors for HIV-1 transmission in women: results from a cohort study." Aids, 1993. 7(1): p. 95-102.
Makarova, K.S., Y.I. Wolf, and E.V. Koonin, "Comparative genomics of defense systems in archaea and bacteria." Nucleic Acids Res, 2013. 41(8): p. 4360-77.
Maltby, R., et al., "Nutritional Basis for Colonization Resistance by Human Commensal *Escherichia coli* Strains HS and Nissle 1917 against *E. coli* O157:H7 in the Mouse Intestine" PLoS One, 2013. 8(1): p. e53957.
Marri, P.R., et al., "Genome Sequencing Reveals Widespread Virulence Gene Exchange among Human *Neisseria* Species" PLoS One, 2010. 5(7): p. e11835.
Merz, A.J. and M. So, "Interactions of pathogenic Neisseriae with epithelial cell membranes." Annu Rev Cell Dev Biol, 2000. 16: p. 423-57.

Miller, K., et al., "Isolation of Neisseria elongata and of Capnocytophaga ochracea from vaginal specimens"J Infect, 1985. 10(2): p. 174-5.
Packiam, M., et al., "Protective role of Toll-like receptor 4 in experimental gonococcal infection of female mice." Mucosal Immunol, 2012. 5(1): p. 19-29.
Peters, R.P., et al., "Screening of oropharynx and anorectum increases prevalence of Chlamydia trachomatis and Neisseria gonorrhoeae infection in female STD clinic visitors." Sex Transm Dis, 2011. 38(9): p. 783-7.
Poland, G.A., "Prevention of meningococcal disease: current use of polysaccharide and conjugate vaccines." Clin Infect Dis, 2010. 50 Suppl 2: p. S45-53.
Ramsey, M.E., et al., "New complementation constructs for inducible and constitutive gene expression in Neisseria gonorrhoeae and Neisseria meningitidis." Appl Environ Microbiol, 2012. 78(9): p. 3068-78.
Royce, R.A., et al., "Sexual transmission of HIV." N Engl J Med, 1997. 336(15): p. 1072-8.
Simms, A.N. and A.E. Jerse, "In Vivo Selection for Neisseria gonorrhoeae Opacity Protein Expression in the Absence of Human Carcinoembryonic Antigen Cell Adhesion Molecules" Infect Immun, 2006. 74(5): p. 2965-74.
Stephens, D.S., "Biology and pahtogenesis of the evolutionarily successful, obligate human bacterium Neisseria menigitidis" Vaccine, 2009. 27 Suppl 2: p. B71-7.
Swanson, J., "Studies on gonococcus infection. IV. Pili: their role in attachment of gonococci to tissue culture cells." J Exp Med, 1973. 137(3): p. 571-89.
Unemo, M. and W.M. Shafer, "Antibiotic resistance in Neisseria gonorrhoeae: origin, evolution, and lessons learned for the future." Ann N Y Arad Sci, 2011. 1230: p. E19-28.
Warner, D.M., et al., "Regulation of the MtrC-MtrD-MtrE efflux-pump system modulates the in vivo fitness of geisseria gonorrhoeae." J Infect Dis, 2007. 196(12): p. 1804-12.
Warner, D.M., et al. "Clinically relevant mutations that cause derepression of the Neisseria gonorrhoeae MtrC-MtrD-MtrE Efflux pump system confer different levels of antimicrobial resistance and in vivo fitness." Mol Microbiol, 2008. 70(2): p. 462-78.
Whiley, D.M., et al., "The ticking time bomb: escalating antibiotic resistance in Neisseria gonorrhoeae is a public health disaster in waiting." J Antimicrob Chemother, 2012. 67(9): p. 2059-61.
Wolfgang, M., et al., "The comP locus of Neisseria gonorrhoeae encodes a type IV prepilin that is dispensable for pilus biogenesis but essential for natural transformation." Mol Microbiol, 1999. 31(5): p. 1345-57.
Wolfgang, W.J., et al., "*Neisseria oralis* sp. nov., isolated from healthy gingival plaque and clinical samples." Int J Syst Evol Microbiol, 2013. 63(Pt 4): p. 1323-8.
Wu, H., et al. "A strain-specific catalase mutation and mutation of the metal-binding transporter gene mntC attenuate Neisseria gonorrhoeae in vivo but not by increasing susceptibility to oxidative killing by phagocytes." Infect Immun, 2009. 77(3): p. 1091-102.
Wu, H.M., et al., "Emergence of ciprofloxacin-resistant Neisseria meningitidis in North America." N Engl J Med, 2009. 360(9): p. 886-92.
Xie, H., et al., "*Streptococcus cristatus* ArcA interferes with Porphyromonas gingivalis pathogenicity in mice." J Periodontal Res, 2012. 47(5): p. 578-83.

* cited by examiner $*p < 0.01, **p < 0.001$

Duration of recovery (clearance) of WT Ngo from mice inoculated with and without Nel Duration of recovery (clearance) of Ngo ΔcomP from mice inoculated with and without Nel Colonization load of WT Ngo in mice inoculated with and without Nel Colonization load of Ngo ΔcomP in mice inoculated with and without Nel

COMPOSITIONS AND METHODS FOR TREATING GONORRHEA

CROSS-REFERENCE TO RELATED APPLICATIONS

The present application is a Section 371 U.S. national stage entry of International Patent Application No. PCT/US2015/048114, International Filing Date Sep. 2, 2015, which claims the benefit of U.S. Provisional Patent Application No. 62/044,776, filed Sep. 2, 2014, the contents of which are incorporated by reference in their entireties.

STATEMENT REGARDING FEDERALLY SPONSORED RESEARCH OR DEVELOPMENT

This invention was made with government support under Grant No. R21 AI111944, awarded by NIH. The government has certain rights in the invention.

FIELD OF THE INVENTION

The present invention relates to compositions and methods for preventing and/or treating gonorrhea. In particular, the present invention provides compositions comprising an effective amount of a commensal species of *Neisseria* (e.g., an effective amount of an extract of a commensal species of *Neisseria*), wherein such compositions are capable of inhibiting the growth of *Neisseria gonorrhoeae*.

BACKGROUND

Gonorrhea, an important public health problem and the second most common notifiable disease in the United States, is a purulent infection of mucous membrane surfaces caused by the gram-negative diplococcus *Neisseria gonorrhoeae*. Although gonorrhea (known colloquially as the clap and the drip) is most frequently spread during sexual contact, it can also be transmitted from the mother's genital tract to the newborn during birth, causing opthalmia neonatorum and systemic neonatal infection.

In women, the cervix and urethra are the most common site of gonorrheal infections. *Neisseria gonorrhoeae* can also spread to other parts of the body to cause infections of the joints (gonococcal arthritis) and Fallopian tubes, which can result in Pelvic inflammatory disease (PID) and ectopic pregnancy. In men, *Neisseria gonorrhoeae* most often causes localized infections of the anterior urethra. In men and women, *Neisseria gonorrhoeae* infections increase susceptibility to human immunodeficiency virus (HIV) infection. Most commonly, the term gonorrhea refers to urethritis and/or cervicitis in a sexually active person.

Gonococcal infections following sexual and perinatal transmission are a major source of morbidity worldwide. In the developed world, where prophylaxis for neonatal eye infection is standard, the vast majority of infections follow genitourinary mucosal exposure.

Improved therapeutic options for treating gonorrhea and/or conditions involving *Neisseria gonorrhoeae* activity are needed.

SUMMARY OF THE INVENTION

Experiments conducted during the course of developing embodiments for the present invention demonstrated that *Neisseria elongata* (Nel) dramatically reduces *Neisseria gonorrhoeae* (Ngo) viability in vitro and in vivo. Specifically, Nel DNA was identified as a lethal agent. Indeed, it was shown that DNA purified from intact Nel cells as well as the Nel DNA in the growth medium were able to kill Ngo. It was concluded that Ngo is killed when it takes up Nel DNA via its Type IV pilus (Tfp) and the 10 base pair DNA Uptake Sequence (DUS) that is present in multiple copies in all neisserial genomes. This conclusion is based on the following data: Ngo mutants deleted of the Tfp-associated genes comP, pilT and pilE (ΔcomP, ΔpilT, ΔpilE) and the recombination gene recA are resistant to killing by Nel DNA. comP is known to encode a protein on Tfp that binds the neisserial DUS, pilT to encode the Tfp motor complex that takes the bound DNA into the bacterial cell, and pilE to encode pilin (PilE), the structural protein of the Tfp fiber. The RecA enzyme recombines incoming neisserial DNA into the Ngo genome. Ngo deleted of any one of these genes is not transformed by neisserial DNA. The conducted animal experiments are consistent with in vitro results. Wild type (WT) Ngo is cleared more quickly from mice when inoculated together with Nel, compared to WT Ngo inoculated alone into animals. In contrast, Nel does not affect the clearance of the Ngo ΔcomP mutant from mice.

Accordingly, in certain embodiments, the present invention provides methods for treatment of a bacterial infection in an individual in need thereof comprising the step of administering to the individual a composition comprising a therapeutically effective amount of a commensal species of *Neisseria* (e.g., an effective amount of an extract of a commensal species of *Neisseria*). In some embodiments, the treatment is ameliorating or prophylactic. In some embodiments, the subject is a mammal (e.g., a human).

In some embodiments, the extract comprises at least a portion of nucleic acid from the commensal species of *Neisseria*. In some embodiments, the at least a portion of nucleic acid is at least a portion of DNA. In some embodiments, the at least a portion of DNA is at least a portion of genomic DNA. In some embodiments, the at least a portion of DNA is at least a portion of chromosomal DNA. In some embodiments, the extract comprises at least a portion of a peptide (linear or cyclic) from the commensal species of *Neisseria*. In some embodiments, the extract comprises at least a portion of a non-proteinaceous organic compound from the commensal species of *Neisseria*.

In some embodiments, the therapeutically effective amount of a commensal species of *Neisseria* (e.g., an effective amount of an extract of a commensal species of *Neisseria*) is administered in the form of a pharmaceutical composition. In some embodiments, a commensal species of *Neisseria* is administered as a probiotic (e.g., the living organism).

In some embodiments, the bacterial infection is caused by *Neisseria gonorrhoeae* (Ngo).

In some embodiments, commensal species of *Neisseria* is selected from the group consisting of *Neisseria elongata* (Nel) and *Neisseria polysaccharea* (Npo).

In some embodiments, the composition is administered to an individual in need thereof by topical, enteral or parenteral administration.

In some embodiments, the composition is co-administered with one or more additional drugs.

In some embodiments, the one or more additional drugs comprise one or more antibiotics.

In certain method for the inhibition of bacterial growth and/or for the killing of bacteria in a product, comprising the step of adding to the product a composition comprising an effective amount of a commensal species of *Neisseria* (e.g., an effective amount of an extract of a commensal species of *Neisseria*), thereby inhibiting bacterial growth and/or killing the bacteria.

In some embodiments, antibacterial composition is selected from the group consisting of a preservative, an antiseptic, a disinfectant, an anti-fouling agent and a medicament. In some embodiments, the antibacterial composition is a preservative in a food product, feed composition, beverage, cosmetics or pharmaceuticals.

In some embodiments, the bacterium is *Neisseria gonorrhoeae* (Ngo).

In some embodiments, the extract comprises at least a portion of nucleic acid from the commensal species of *Neisseria*. In some embodiments, the at least a portion of nucleic acid is at least a portion of DNA. In some embodiments, the at least a portion of DNA is at least a portion of genomic DNA. In some embodiments, the at least a portion of DNA is at least a portion of chromosomal DNA. In some embodiments, the extract comprises at least a portion of a peptide (linear or cyclic) from the commensal species of *Neisseria*. In some embodiments, the extract comprises at least a portion of a non-proteinaceous organic compound from the commensal species of *Neisseria*.

In some embodiments, the commensal species of *Neisseria* is selected from the group consisting of *Neisseria elongata* (Nel) and *Neisseria polysaccharea* (Npo).

In certain embodiments, the present invention provides pharmaceutical compositions comprising an effective amount of a commensal species of *Neisseria* (e.g., an effective amount of an extract of a commensal species of *Neisseria*) and a pharmaceutically acceptable carrier. In some embodiments, the commensal species of *Neisseria* is selected from the group consisting of *Neisseria elongata* (Nel) and *Neisseria polysaccharea* (Npo). In some embodiments, the extract comprises at least a portion of nucleic acid from the commensal species of *Neisseria*. In some embodiments, the at least a portion of nucleic acid is at least a portion of DNA. In some embodiments, at least a portion of DNA is at least a portion of genomic DNA. In some embodiments, at least a portion of DNA is at least a portion of chromosomal DNA. In some embodiments, the extract is the entire live organism (e.g., in the form of a probiotic).

In some embodiments, the pharmaceutical composition further comprises agents configured to inhibit sperm activity.

In certain embodiments, the present invention provides compositions comprising at least a portion of a gene product capable of inhibiting bacterial growth and/or killing said bacteria, wherein the gene product is encoded by nucleic acid expressed in a commensal species of *Neisseria*. In some embodiments, the bacterium is *Neisseria gonorrhoeae* (Ngo). In some embodiments, nucleic acid is DNA. In some embodiments, the DNA is genomic DNA. In some embodiments, the DNA is chromosomal DNA. In some embodiments, the commensal species of *Neisseria* is selected from the group consisting of *Neisseria elongata* (Nel) and *Neisseria polysaccharea* (Npo). In some embodiments, the gene product is a polypeptide, a lipid, an amino acid sequence, a sugar, or a non-proteinaceous molecule.

In certain embodiments, the present invention provides compositions comprising nucleic acid capable of inhibiting bacterial growth and/or killing said bacteria upon exposure with the bacteria, wherein the nucleic acid is expressed in a commensal species of *Neisseria*. In some embodiments, the bacteria is *Neisseria gonorrhoeae* (Ngo). In some embodiments, the nucleic acid is DNA. In some embodiments, the DNA is genomic DNA. In some embodiments, the DNA is chromosomal DNA. In some embodiments, the commensal species of *Neisseria* is selected from the group consisting of *Neisseria elongata* (Nel) and *Neisseria polysaccharea* (Npo). In some embodiments, the gene product is a polypeptide (linear or cyclic) or a non-proteinaceous compound.

BRIEF DESCRIPTION OF THE DRAWINGS

(FIG. 5A) Average colonization load of Ngo and Nel. CFU/ml: colony forming units. The difference in Ngo colonization load between mice inoculated with Ngo alone and mice inoculated with Ngo and Nel was statistically significant ($P<0.021$ repeated measures ANOVA). (FIG. 5B) Percent of mice colonized with Ngo in the presence or absence of Nel (measure of clearance). Kaplan Meier colonization curves showing faster clearance of Ngo from mice co-inoculated with Nel ($P\leq0.003$, log rank test).

(FIG. 6A) The vagina of mice were inoculated with WT Ngo alone or WT Ngo and Nel in a 50:50 ratio, and Ngo counts were measured over the course of 7 days. Percent of mice colonized with WT Ngo when Nel is present (orange line) or absent (red line). ($P=0.0333$ log rank test). (FIG. 6B) The vagina of mice were inoculated with Ngo ΔcomP alone or Ngo ΔcomP and Nel in a 50:50 ratio, and Ngo ΔcomP counts were measured over the course of 7 days. Percent of mice colonized with Ngo DcomP when Nel is present (brown line) or absent (green line). ($P=0.2509$ log rank test; not statistically significant.) These results indicate that the susceptibility of Ngo to Nel clearance from mice requires its ability to take up neisserial DNA.

FIG. 7A and FIG. 7B show the colonization load data (number of viable bacteria) recovered from the inoculated mice described in FIG. 6a. FIG. 7A shows the number of WT Ngo MS11 recovered from mice inoculated with or without Nel; FIG. 7B shows the number of Ngo MS11 ΔcomP recovered from mice inoculated with or without Nel. The data are expressed as Colony Forming Units/mL (CFU/mL) averaged for all mice (left), and as the Geometric Mean of the bacterial counts (right).

DETAILED DESCRIPTION

Figure 1:
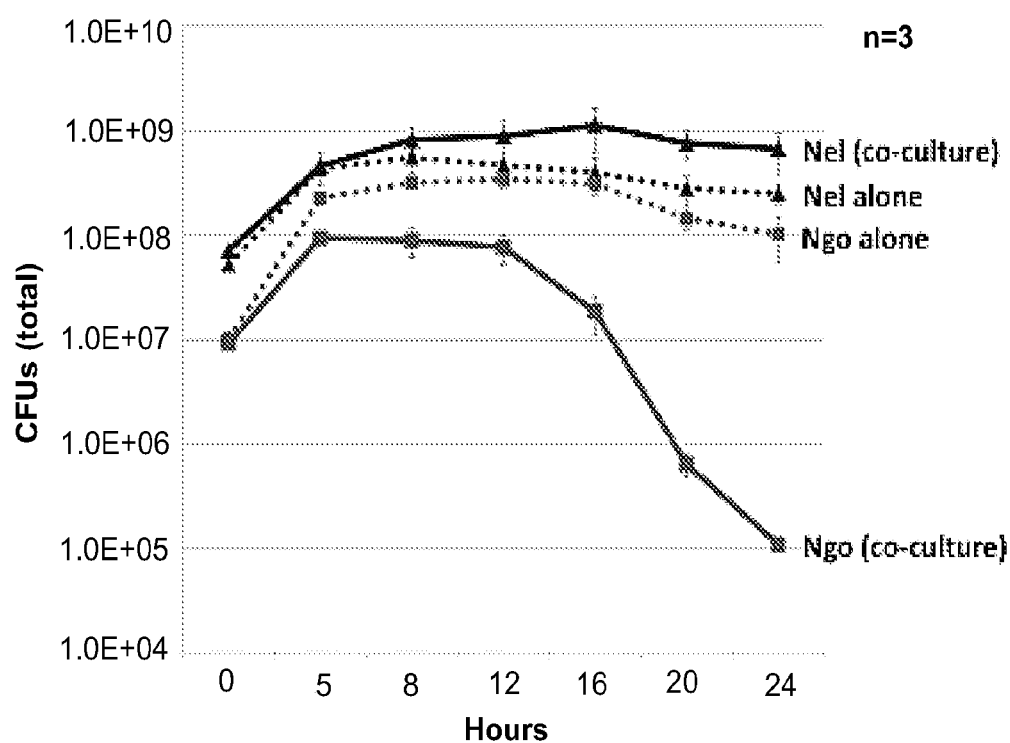
FIG. 1 shows Nel reduces the viability of Ngo during co-culture in vitro. Values and SEM were calculated from three independent experiments.

At least 16 species of *Neisseria* have been isolated from humans (e.g., *N. bacilliformis, N. cinerea, N. denitrificans, N. elongata, N. flavescens, N. gonorrhoeae, N. lactamica, N. macacae, N. meningitidis, N. mucosa, N. pharyngis, N. polysaccharea* (Npo), *N. sicca, N. subflava*). Two of these are pathogens, *Neisseria gonorrhoeae* (Ngo) and *Neisseria meningitidis* (Nme); the others are commensals that form part of the normal flora (see, e.g., Knapp, J. S. et al, J Clin Microbiol, 1988. 26(5): p. 896-900; Wolfgang, W. J., et al., Int J Syst Evol Microbiol, 2013. 63(Pt 4): p. 1323-8) (e.g., *Neisseria bacilliformis, Neisseria cinerea, Neisseria elongata, Neisseria flavescens, Neisseria lactamica, Neisseria mucosa, Neisseria polysaccharea, Neisseria sicca, Neisseria subflava, Neisseria flava*). 106 million new cases of gonorrhea occur each year, worldwide (see, e.g., Gerbase, A., et al., Sex Transm Dis, 2000. 15). Ngo primarily causes urogenital tract (UGT) infections; it is also found in the oropharynx of patients or partners of patients with UGT gonorrhea (see, e.g., Hobbs, M. M., et al., Front Microbiol, 2011. 2: p. 123; Peters, R. P., et al., Sex Transm Dis, 2011. 38(9): p. 783-7). Persistent infection can lead to such serious complications as salpingitis, pelvic inflammatory disease and ectopic pregnancy. There is a strong epidemiological link between gonorrhea and HIV/AIDs (see, e.g., Laga, M., et al., Aids, 1993. 7(1): p. 95-102; Royce, R. A., et al., N Engl J Med, 1997. 336(15): p. 1072-8). Antibiotics are the mainstay of infection control, as vaccine development is hampered by antigenic variation of bacterial surface components (see, e.g., Hobbs, M. M., et al., Front Microbiol, 2011. 2: p. 123). However, Ngo has acquired resistance to all antibiotics recommended for its treatment, and it is now considered a "ticking time bomb" (see, e.g., Whiley, D. M., et al., J Antimicrob Chemother, 2012. 67(9): p. 2059-61; Unemo, M. and W. M. Shafer, Ann N Y Acad Sci, 2011. 1230: p. E19-28). Nme asymptotically colonizes the upper respiratory tract and causes disease when it crosses the epithelial and/or endothelial barriers (see, e.g., Stephens, D. S., Vaccine, 2009. 27 Suppl 2: p. B71-7). Infection is often fatal unless treated quickly with antibiotics. Vaccines have dramatically lowered the incidence of Nme infection (see, e.g., Poland, G. A., Clin Infect Dis, 2010. 50 Suppl 2: p. S45-53). As these vaccines do not protect against all serogroups, efforts to improve coverage are ongoing.

Commensal species of *Neisseria* receive little attention because they rarely cause disease. Currently, PubMed lists 294 publications on these organisms, and >20,000 on Ngo and Nme. Commensal *Neisseria* are known to colonize the oropharynx (see, e.g., Knapp, J. S. et al, J Clin Microbiol, 1988. 26(5): p. 896-900; Han, X. Y., T. Hong, and E. Falsen, J Clin Microbiol, 2006. 44(2): p. 474-9; Cartwright, K. A., et al., Epidemiol Infect, 1987. 99(3): p. 591-601); they also colonize other sites, including the vagina (see, e.g., Miller, K., et al., J Infect, 1985. 10(2): p. 174-5; Aagaard, K., et al., PLoS One, 2012. 7(6): p. e36466). Widespread horizontal gene transfer (HGT) has occurred among commensal and pathogenic *Neisseria* (see, e.g., Wu, H. M., et al., N Engl J Med, 2009. 360(9): p. 886-92; Marri, P. R., et al., PLoS One, 2010. 5(7): p. e11835), supporting the epidemiological evidence that these two groups of bacteria can inhabit similar niches. Whether they interact with each other when in proximity is unknown.

Some commensal bacteria have the ability to inhibit pathogen colonization. In mouse models of infection, *Lactobacillus rhamnosum* and *Lactobacillus acidophilus* reduce *Citrobacter rodentium* colonization in the gut (see, e.g., Johnson-Henry, K. C., et al., J Infect Dis, 2005. 191(12): p. 2106-17). *Streptococcus cristatus* attenuates *Porphyromonas gingivalis* colonization in the oral cavity (see, e.g., Xie, H., et al., J Periodontal Res, 2012. 47(5): p. 578-83); and *E. coli* biotype Nissle 1917, which has been used as a probiotic in Europe since the 1920s, prevents *E. coli* O157:H7 colonization in the gut (see, e.g., Maltby, R., et al., PLoS One, 2013. 8(1): p. e53957). In vitro, Nissle 1917 outperforms and outcompetes pathogenic *E. coli* in biofilm formation (see, e.g., Hancock, V., M. Dahl, and P. Klemm, J Med Microbiol, 2010. 59(Pt 4): p. 392-9). *Streptococcus epidermidis* is also better at forming biofilms than *Streptococcus aureus*, and secretes a protease that dissolves pathogen biofilms, rendering the bacteria more susceptible to antibiotics (see, e.g., Iwase, T., et al., Nature, 2010. 465(7296): p. 346-9). Environmental microbes also exhibit such antagonistic behavior. Commensal *Exiguobacterium* spp inhibits colonization of coral by opportunist *Serratia marcescens* (see, e.g., Krediet, C. J., et al., ISME J, 2013. 7(5): p. 980-90). The mechanisms by which commensals inhibit pathogen colonization are largely unknown; there is much interest in identifying these mechanisms because of the implications for therapy.

Experiments conducted during the course of developing embodiments for the present invention involved in vitro and in vivo approaches to determine whether the commensal, *Neisseria elongata* (Nel), antagonizes pathogen Ngo. Nel was found to dramatically reduce the viability of one lab strain and three recent clinical isolates of Ngo in vitro. Strikingly, the susceptibility of Ngo to killing by Nel required its uptake of Nel genomic DNA. Experiments using the mouse model for Ngo colonization and persistence replicated this in vitro antagonistic behavior: Ngo is cleared from mice more rapidly when Nel is present.

Figure 2:
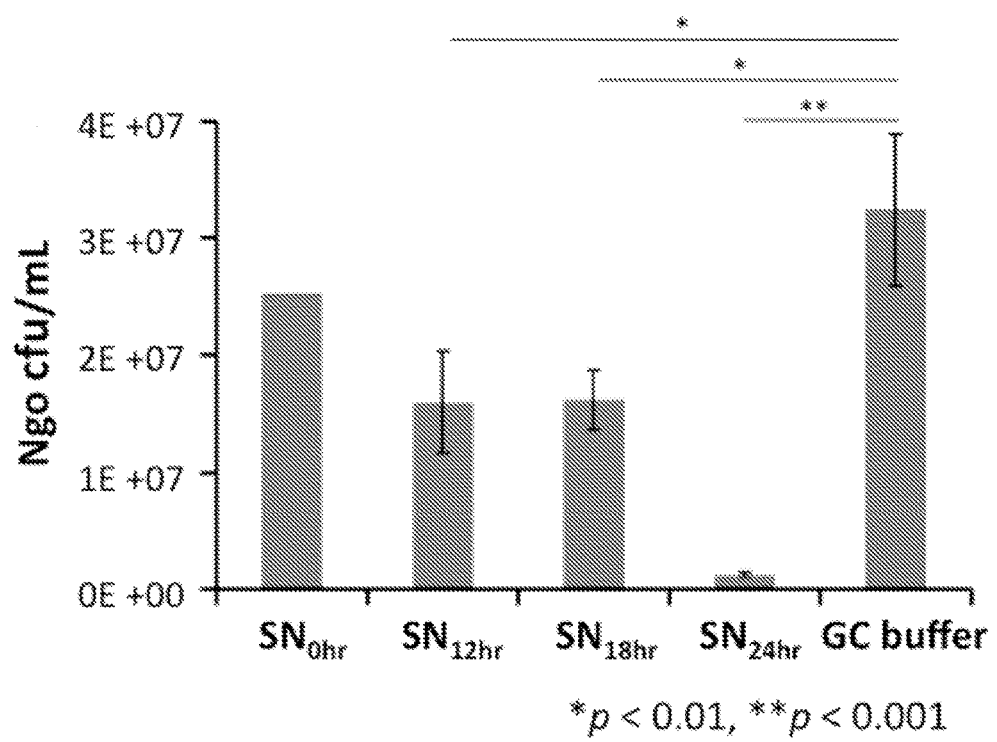
FIG. 2 shows Nel supernates reduce Ngo viability. Values, Standard Deviation and P values were calculated from three independent experiments. SN: supernate. GC buffer: media used to grow Nel. cfu/mL: colony forming units per ml of mixture. $*p<0.01$, $**p<0.001$, Student's t-test.
Figure 3:
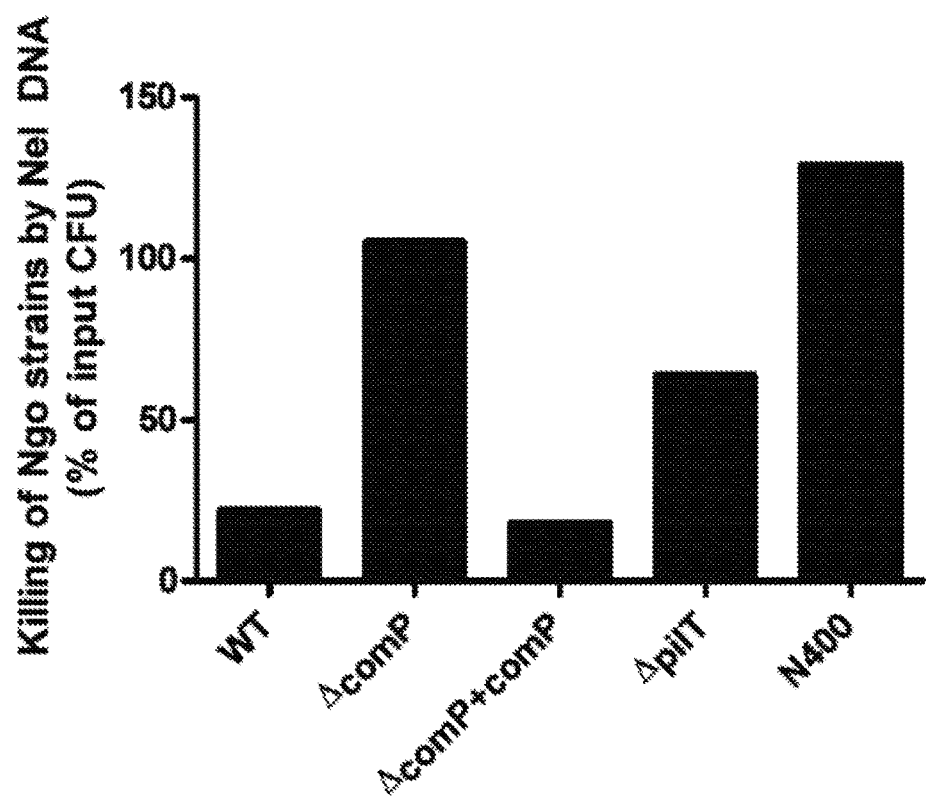
FIG. 3: Killing of Ngo strains by Nel DNA. WT and mutant Ngo were incubated with 20 ug/mL of purified Nel DNA for 4 hours, and the number of surviving Colony Forming Units (CFU) were expressed as a percent of input CFUs. WT: wild type Ngo. ΔcomP: Ngo mutant deleted of the comP gene and unable to take up neisserial DNA. ΔcomP+comP: the ΔcomP mutant complemented with a WT copy of comP. ΔpilT: Ngo mutant deleted of the pilT gene that encodes the Tfp retraction motor and cannot take up neisseria DNA. N400: Ngo mutant that cannot recombine the DNA taken up into the cell. These results indicate that WT Ngo is readily killed by Nel DNA, but Ngo mutants which cannot take up neisserial DNA are resistant to killing by Nel DNA.

Specifically, results from such experiments demonstrate that Ngo is killed when cultured in the presence of Nel (FIG. 1). Furthermore, Ngo is killed by the spent medium in which Nel was grown (FIG. 1), and by Nel DNA purified away from protein and RNA (FIG. 3). Such experiments also demonstrate that Ngo mutants ΔcomP, ΔpilT or ΔpilE, which cannot take up neisserial DNA, and Ngo mutant recA, which cannot recombine incoming neisserial DNA into the genome, are resistant to killing by Nel DNA (FIG. 2). Studies have shown that comP encodes the Tfp-associated protein that binds the DUS in neisserial DNA, pilT encodes the PilT motor complex that allows Ngo to take up the bound DNA into the bacterial cell, pilE encodes pilin, the structural subunit of the Tfp fiber.

Figure 4:
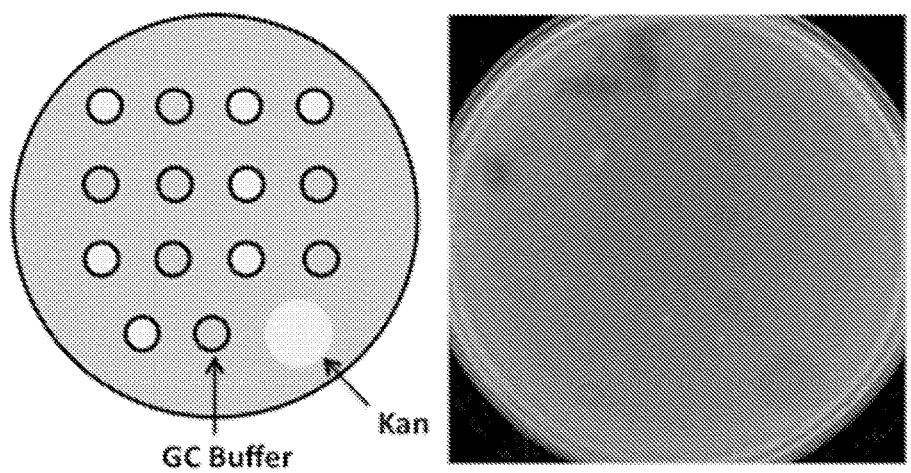
FIG. 4: Agar plate assay developed for detecting killing of Ngo by Nel supernate. Left: Diagram of an agar plate on which extracts from Nel were spotted on a lawn of Ngo cells. Circles indicate the location of the spotted extracts. Lighter circles indicate extracts that killed Ngo cells. Darker circles indicate extracts that failed to kill Ngo cells. GC buffer: media for growing *Neisseria* spotted on the lawn as a negative control (no killing of Ngo). Kan: Kanamycin spotted on the lawn as a positive control (Ngo killed).
Figure 8:
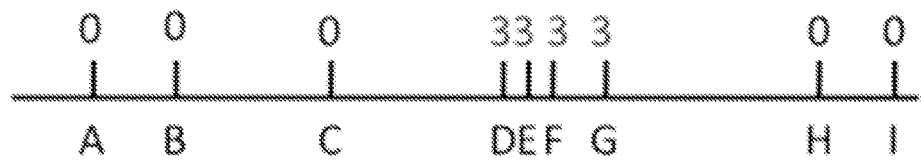
FIG. 8: Diagram of a hypothetical region of Nel DNA (solid line). Shown below are cut sites for hypothetical restriction enzymes A-I. Shown above are scores for restriction enzymes A-I based on their ability to abolish the killing activity of Nel DNA against Ngo; a score of 3 indicates maximal killing activity and a score of 0 indicates no killing activity.

Results from these in vitro experiments are recapitulated in animals. Ngo is cleared from mice more quickly when inoculated with Nel into the animals, compared to Ngo inoculated alone (FIG. 4). Importantly, one key Ngo mutant, Ngo ΔcomP, which cannot take up neisserial DNA, is cleared at the same rate whether Nel is present or not (FIG. 8). These results indicate that clearance of Ngo from the mouse is due to its killing by Nel, and requires its ability to take up Nel DNA.

Thus, in certain embodiments, the present invention provides compositions comprising an effective amount of a commensal species of *Neisseria* (e.g., an effective amount of an extract of a commensal species of *Neisseria*). In some embodiments, the extract of a commensal species of *Neisseria* is capable of inhibiting the growth of Ngo and/or is capable of killing Ngo. Examples of commensal species of *Neisseria* capable of killing Ngo and/or inhibiting the growth of Ngo include, but are not limited to Nel and N *polysaccharea* (Npo).

Such compositions are not limited to a particular type of extract of the commensal species of *Neisseria* capable of inhibiting the growth of Ngo and/or is capable of killing Ngo. In some embodiments, the extract is one or more polypeptides (e.g., 1, 2, 3, 4, 5, 6, 7, 8, 10, 20, 200, 2000, 9999, etc.) of the respective commensal *Neisseria* species. In some embodiments, the extract is one or more gene products of the respective commensal *Neisseria* species. In some embodiments, the extract includes at least a portion of nucleic acid of the respective commensal *Neisseria* species. In some embodiments, the extract includes one or more specific DNA loci of the respective commensal *Neisseria* species. In some embodiments, the extract includes at least a portion of genomic DNA of the respective commensal *Neisseria* species. In some embodiments, the extract includes at least a portion of chromosomal DNA of the respective commensal *Neisseria* species. In some embodiments, the extract is the entire live organism (e.g., in the form of a probiotic).

The compositions of the present invention can be prepared from a *Neisseria* species by any method suitable for obtaining a composition capable of inhibiting the growth of Ngo and/or killing Ngo. For example, in some embodiments, a sample having a particular strain of *Neisseria* (Nel) (or portion thereof) is provided and one or more purification steps and/or isolation steps and/or concentration steps resulting in purification and/or isolation and/or concentration from the sample a composition having an extract of the commensal species of *Neisseria* capable of inhibiting the growth of Ngo and/or killing Ngo.

Such compositions are not limited to particular uses. In some embodiments, the compositions are capable of a static action wherein Ngo growth is inhibited. In some embodiments, the compositions are capable of a cidal action wherein Ngo organisms are killed. In some embodiments, the compositions are capable of a lytic action wherein Ngo organisms are killed and lysed.

In some embodiments, such compositions are heat stable (e.g., retains desired activity at any temperature for any desired amount of time).

In some embodiments, the composition is an antiseptic. Antiseptics are antimicrobial substances that are applied to living tissue/skin to reduce the possibility of infection and/or sepsis, and/or putrefaction. Antiseptics are generally distinguished from antibiotics by their ability to be transported through the lymphatic system to destroy bacteria within the body, and from disinfectants, which destroy microorganisms found on non-living objects. In some embodiments, antiseptic compositions comprising an effective amount of a commensal species of *Neisseria* (e.g., an effective amount of an extract of a commensal species of *Neisseria*) (e.g., Nel, Npo) capable of inhibiting the growth of Ngo and/or is killing Ngo are provided. For example, in some embodiments, such an antiseptic composition can be applied to the tissue of a subject (e.g., a human subject) for purposes of preventing the growth or inducing the killing of Ngo.

In some embodiments, the composition is a disinfectant. In some embodiments, disinfectant compositions comprising an effective amount of a commensal species of *Neisseria* (e.g., an effective amount of an extract of a commensal species of *Neisseria*) (e.g., Nel, Npo) capable of inhibiting the growth or of inducing the killing of Ngo are provided. For example, in some embodiments, such a disinfectant composition can be used in the cleaning of hospitals such as in cleaning of an operating room and/or surgery equipment. Disinfectants should generally be distinguished from antibiotics that destroy microorganisms within the body, and from antiseptics, which destroy microorganisms on living tissue.

In some embodiments, the compositions are used for anti-fouling. Anti-fouling is the process of removing or inhibiting the accumulation of biofouling. Biofouling or biological fouling is the undesirable accumulation of microorganisms, plants, algae, and animals on surfaces.

In some embodiments, the present invention relates to a pharmaceutical composition comprising an effective amount of a commensal species of *Neisseria* (e.g., an effective amount of an extract of a commensal species of *Neisseria*) (e.g., Nel, Npo) capable of inhibiting the growth or inducing the killing of Ngo. In some embodiments, the pharmaceutical composition comprises the entire live organism (e.g., the entire commensal species of *Neisseria*) (e.g., in the form of a probiotic). In some embodiments, such pharmaceutical compositions can be used as a medicament (e.g., for purposes of treating a subject having gonorrhea and/or any condition involving the presence of Ngo). In some embodiments, the treatment can be ameliorating, curative or prophylactic treatment of gonorrhea and/or any condition involving the presence of Ngo.

The individual treated can be a human being or an animal. The animal can be a dog, cat, horse, rabbit, hamster, mouse, rat, monkey, cow, pig, donkey, fish, bird, reptile or any other animal in need of treatment. In one embodiment the animal is a laboratory/test animal. In another embodiment the animal in need of treatment is a pet or livestock such as domesticated cows, pigs, sheep, poultry or farmed fish.

The human being can be a man, a woman, a postmenopausal women, a pregnant woman, a lactating woman, an infant, a child, or an adult. The individual such as a human being can be of any age such as from newborn to 120 years old, for example from 0 to 6 months, such as from 6 to 12 months, for example from 1 to 5 years, such as from 5 to 10 years, for example from 10 to 15 years, such as from 15 to 20 years, for example from 20 to 25 years, such as from 25 to 30 years, for example from 30 to 35 years, such as from 35 to 40 years, for example from 40 to 45 years, such as from 45 to 50 years, for example from 50 to 60 years, such as from 60 to 70 years, for example from 70 to 80 years, such as from 80 to 90 years, for example from 90 to 100 years, such as from 100 to 110 years, for example from 110 to 120 years.

In certain embodiments, methods for treating human subjects having gonorrhea are provided. In such embodiments, pharmaceutical compositions comprising an effective amount of a commensal species of *Neisseria* (e.g., an effective amount of an extract of a commensal species of *Neisseria*) (e.g., Nel, Npo) capable of inhibiting the growth or inducing the killing of Ngo are administered to such a human subject resulting the inhibition of and/or killing of Ngo.

In certain embodiments, methods for preventing human subjects from developing gonorrhea are provided. In such embodiments, pharmaceutical compositions comprising an effective amount of a commensal species of *Neisseria* (e.g., an effective amount of an extract of a commensal species of *Neisseria*) (e.g., Nel, Npo) capable of inhibiting the growth or inducing the killing of Ngo are administered to such a human subject resulting the inhibition or killing of Ngo exposed to the subject.

Such compositions may be administered using one or more of the following routes of administration. Indeed, routes of administration can broadly be divided into: Topical: local effect, substance is applied directly where its action is desired; Enteral: desired effect is systemic (non-local), substance is given via the digestive tract; Parenteral: desired effect is systemic, substance is given by routes other than the digestive tract.

Topical administration includes Epicutaneous (application onto the skin), Inhalational, Enema, Eye drops (onto the conjunctiva), Ear drops, Intranasal route (into the nose), and Vaginal.

Enteral administration is any form of administration that involves any part of the gastrointestinal tract and includes by mouth (peroral), by gastric feeding tube, duodenal feeding tube, or gastrostomy, and/or rectally.

Parenteral by injection or infusion include Intravenous (into a vein), Intraarterial (into an artery), Intramuscular (into a muscle), Intracerebral (into the cerebrum) direct injection into the brain, Intracerebroventricular (into the cerebral ventricles) administration into the ventricular system of the brain, Intracardiac (into the heart), Subcutaneous (under the skin), Intraosseous infusion (into the bone marrow) is, in effect, an indirect intravenous access because the bone marrow drains directly into the venous system, Intradermal, (into the skin itself), Intrathecal (into the spinal canal), Intraperitoneal, (infusion or injection into the peritoneum), Intravesical infusion is into the urinary bladder, and Intracavernosal injection is into the base of the penis. Other parenteral administration modes include Transdermal (diffusion through the intact skin), Transmucosal (diffusion through a mucous membrane), e.g. insufflation, sublingual, i.e. under the tongue, vaginal suppositories, Inhalational, Intracisternal: given between the first and second cervical vertebrae, Other epidural (synonym: peridural) (injection or infusion into the epidural space), and Intravitreal, through the eye.

Peroral intake may be in the form of Tablets, Capsules, Mixtures, Liquid, and Powder.

Injections may be either systemic or local injections.

Other administration modes of the present invention include Jet-infusion (micro-drops, micro-spheres, micro-beads) through skin, Drinking solution, suspension or gel, Inhalation, Nose-drops, Eye-drops, Ear-drops, Skin application as ointment, gel, lotion, cream or through a patch, Vaginal application as ointment (e.g., via condum, spermacide ointment, etc.), gel, crème or washing, Gastro-Intestinal flushing, and Rectal washings or by use of suppositories.

Administration can be performed as a single administration such as single intake, injection, application, washing; multiple administrations such as multiple intakes, injections, applications, washings; on a single day basis or over prolonged time as days, month, years.

A dose or dosage of the composition according to the present invention may be given as a single dose or in divided doses. A single dose occurs only once, with the drug administered either as a bolus or by continuous infusion. Alternatively, the dose may be divided into multiple doses and given recurrently, such as twice (two times), for example three times, such as four times, for example five times, such as six times, for example seven times, such as eight times, for example nine times, such as ten divided doses. Furthermore, the dose may be given repeatedly, i.e. more than once, such as twice (two times), for example three times, such as four times, for example five times, such as six times, for example seven times, such as eight times, for example nine times, such as ten times a day. Alternatively, the dose may be in sustained release form. A bolus is in theory regarded as given immediately, and should be administered in less than 5 minutes.

It follows that the composition according to the present invention may be given once or more daily, or alternatively may be given with intervals of 1 day, such as 2 days, for example 3 days, such as 4 days, such as 5 days, for example 6 days, such as 7 days (1 week), for example 8 days, such as 9 days, such as 10 days, for example 11 days, such as 12 days, for example 13 days, such as 14 days (2 weeks), such as 3 weeks, for example 4 weeks, such as 5 weeks, for example 6 weeks, such as 7 weeks, such as 8 weeks, for example 12 weeks.

The composition according to the present invention is given in an effective amount to an individual in need thereof. The amount of composition according to the present invention in one preferred embodiment is in the range of from about 0.01 milligram per kg body weight per dose to about 1000 milligram per kg body weight per dose. In some embodiments, the effective amount is the amount necessary for the composition to induce Ngo growth inhibition and/or killing of Ngo.

The composition according to the present invention can be co-administered to an individual in need thereof in combination with one or more drugs such as one or more drugs with antibacterial effect. The one or more antibiotics can be selected from the group consisting of Amikacin disulfate salt, Amikacin hydrate, Anisomycin from *Streptomyces griseolus*, Apramycin sulfate salt, Azithromycin, Blasticidine S hydrochloride, Brefeldin A, Brefeldin A from *Penicillium brefeldianum*, Butirosin sulfate salt, Butirosin A from *Bacillus vitellinus*, Chloramphenicol, Chloramphenicol base, Chloramphenicol succinate sodium salt, Chlortetracycline hydrochloride, Chlortetracycline hydrochloride from *Streptomyces aureofaciens*, Clindamycin 2-phosphate, Clindamycin hydrochloride, Clotrimazole, Cycloheximide from microbial, Demeclocycline hydrochloride, Dibekacin sulfate salt, Dihydrostreptomycin sesquisulfate, Dihydrostreptomycin solution, Doxycycline hyclate, Duramycin from *Streptoverticillium cinnamoneus*, Emetine dihydrochloride hydrate), Erythromycin, Erythromycin USP, Erythromycin powder, Erythromycin, Temephos, Erythromycin estolate, Erythromycin ethyl succinate, Erythromycin standard solution, Erythromycin stearate, Fusidic acid sodium salt, G 418 disulfate salt, G 418 disulfate salt powder, G 418 disulfate salt solution liquid, Gentamicin solution liquid, Gentamicin solution, Gentamicin sulfate *Micromonospora purpurea*, Gentamicin sulfate salt, Gentamicin sulfate salt powder USP, Gentamicin-Glutamine solution liquid, Helvolic acid from *Cephalosporium caerulens*, Hygromycin B *Streptomyces hygroscopicus*, Hygromycin B *Streptomyces hygroscopicus* powder, Hygromycin B solution *Streptomyces hygroscopicus*, Josamycin, Josamycin solution, Kanamycin B sulfate salt, Kanamycin disulfate salt from *Streptomyces kanamyceticus*, Kanamycin monosulfate from *Streptomyces kanamyceticus*, Kanamycin monosulfate from *Streptomyces kanamyceticus* powder USP, Kanamycin solution from *Streptomyces kanamyceticus*, Kirromycin from *Streptomyces collinus*, Lincomycin hydrochloride, Lincomycin standard solution, Meclocycline sulfosalicylate salt, Mepartricin, Midecamycin from *Streptomyces mycarofaciens*, Minocycline hydrochloride crystalline, Neomycin solution, Neomycin trisulfate salt hydrate, Neomycin trisulfate salt hydrate powder, Neomycin trisulfate salt hydrate USP powder, Netilmicin sulfate salt, Nitrofurantoin crystalline, Nourseothricin sulfate, Oleandomycin phosphate salt, Oleandomycin triacetate, Oxytetracycline dihydrate, Oxytetracycline hemicalcium salt, Oxytetracycline hydrochloride, Paromomycin sulfate salt, Puromycin dihydrochloride from *Streptomyces alboniger*, Rapamycin from *Streptomyces hygroscopicus*, Ribostamycin sulfate salt, Rifampicin, Rifamycin SV sodium salt, Rosamicin *Micromonospora rosaria*, Sisomicin sulfate salt, Spectinomycin dihydrochloride hydrate, Spectinomycin dihydrochloride hydrate powder, Spectinomycin dihydrochloride pentahydrate, Spiramycin, Spiramycin from *Streptomyces* sp., Spiramycin solution, Streptomycin solution, Streptomycin sulfate salt, Streptomycin sulfate salt powder, Tetracycline, Tetracycline hydrochloride, Tetracycline hydrochloride USP, Tetracycline hydrochloride powder, Thiamphenicol, Thiostrepton from *Streptomyces azureus*, Tobramycin, Tobramycin sulfate salt, Tunicamycin $A_1$ homolog, Tunicamycin $C_2$ homolog, Tunicamycin *Streptomyces* sp., Tylosin solution, Tylosin tartrate, Viomycin sulfate salt, Virginiamycin $M_1$, (S)-(+)-Camptothecin, 10-Deacetylbaccatin III from *Taxus baccata*, 5-Azacytidine, 7-Aminoactinomycin D, 8-Quinolinol crystalline, 8-Quinolinol hemisulfate salt crystalline, 9-Dihydro-13-acetylbaccatin III from *Taxus canadensis*, Aclarubicin, Aclarubicin hydrochloride, Actinomycin D from *Streptomyces* sp., Actinomycin I from *Streptomyces antibioticus*, Actinomycin V from *Streptomyces antibioticus*, Aphidicolin *Nigrospora sphaerica*, Bafilomycin A1 from *Streptomyces griseus*, Bleomycin sulfate from *Streptomyces verticillus*, Capreomycin sulfate from *Streptomyces capreolus*, Chromomycin $A_3$ *Streptomyces griseus*, Cinoxacin, Ciprofloxacin BioChemika, cis-Diammineplatinum(II) dichloride, Coumermycin A1, Cytochalasin B *Helminthosporium dematioideum*, Cytochalasin D *Zygosporium mansonii*, Dacarbazine, Daunorubicin hydrochloride, Daunorubicin hydrochloride USP, Distamycin A hydrochloride from *Streptomyces distallicus*, Doxorubicin hydrochloride, Echinomycin, Echinomycin BioChemika, Enrofloxacin BioChemika, Etoposide, Etoposide solid, Flumequine, Formycin, Fumagillin from *Aspergillus fumigatus*, Ganciclovir, Gliotoxin from *Gliocladium fimbriatum*, Lomefloxacin hydrochloride, Metronidazole purum, Mithramycin A from *Streptomyces plicatus*, Mitomycin C *Streptomyces caespitosus*, Nalidixic acid, Nalidixic acid sodium salt, Nalidixic acid sodium salt powder, Netropsin dihydrochloride hydrate, Nitrofurantoin, Nogalamycin from *Streptomyces nogalater*, Nonactin from *Streptomyces tsusimaensis*, Novobiocin sodium salt, Ofloxacin, Oxolinic acid, Paclitaxel from *Taxus yannanensis*, Paclitaxel from *Taxus brevifolia*, Phenazine methosulfate, Phleomycin *Streptomyces verticillus*, Pipemidic acid, Rebeccamycin from *Saccharothrix aerocolonigenes*, Sinefungin, Streptonigrin from *Streptomyces flocculus*, Streptozocin, Succinylsulfathiazole, Sulfadiazine, Sulfadimethoxine, Sulfaguanidine purum, Sulfamethazine, Sulfamonomethoxine, Sulfanilamide, Sulfaquinoxaline sodium salt, Sulfasalazine, Sulfathiazole sodium salt, Trimethoprim, Trimethoprim lactate salt, Tubercidin from *Streptomyces tubercidicus*, 5-Azacytidine, Cordycepin, Formycin A, (+)-6-Aminopenicillanic acid, 7-Aminodesacetoxycephalosporanic acid, Amoxicillin, Ampicillin, Ampicillin sodium salt, Ampicillin trihydrate, Ampicillin trihydrate USP, Azlocillin sodium salt, Bacitracin *Bacillus licheniformis*, Bacitracin zinc salt *Bacillus licheniformis*, Carbenicillin disodium salt, Cefaclor, Cefamandole lithium salt, Cefamandole nafate, Cefamandole sodium salt, Cefazolin sodium salt, Cefinetazole sodium salt, Cefoperazone sodium salt, Cefotaxime sodium salt, Cefsulodin sodium salt, Cefsulodin sodium salt hydrate, Ceftriaxone sodium salt, Cephalexin hydrate, Cephalosporin C zinc salt, Cephalothin sodium salt, Cephapirin sodium salt, Cephradine, Cloxacillin sodium salt, Cloxacillin sodium salt monohydrate, D-{tilde over ( )}( )-Penicillamine hydrochloride, D-Cycloserine microbial, D-Cycloserine powder, Dicloxacillin sodium salt monohydrate, D-Penicillamine, Econazole nitrate salt, Ethambutol dihydrochloride, Lysostaphin from *Staphylococcus staphylolyticus*, Moxalactam sodium salt, Nafcillin sodium salt monohydrate, Nikkomycin, Nikkomycin Z *Streptomyces tendae*, Nitrofurantoin crystalline, Oxacillin sodium salt, Penicillic acid powder, Penicillin G potassium salt, Penicillin G potassium salt powder, Penicillin G potassium salt, Penicillin G sodium salt hydrate powder, Penicillin G sodium salt powder, Penicillin G sodium salt, Phenethicillin potassium salt, Phenoxymethylpenicillinic acid potassium salt, Phosphomycin disodium salt, Pipemidic acid, Piperacillin sodium salt, Ristomycin monosulfate, Vancomycin hydrochloride from *Streptomyces orientalis*, 2-Mercaptopyridine N-oxide sodium salt, 4-Bromocalcimycin A23187 BioChemika, Alamethicin *Trichoderma viride*, Amphotericin B *Streptomyces* sp., Amphotericin B preparation, Calcimycin A23187, Calcimycin A23187 hemi(calcium-magnesium) salt, Calcimycin A23187 hemicalcium salt, Calcimycin A23187 hemimagnesium salt, Chlorhexidine diacetate salt monohydrate, Chlorhexidine diacetate salt hydrate, Chlorhexidine digluconate, Clotrimazole, Colistin sodium methanesulfonate, Colistin sodium methanesulfonate from *Bacillus colistinus*, Colistin sulfate salt, Econazole nitrate salt, Hydrocortisone 21-acetate, Filipin complex *Streptomyces filipinensis*, Gliotoxin from *Gliocladium fimbriatum*, Gramicidin A from *Bacillus brevis*, Gramicidin C from *Bacillus brevis*, Gramicidin from *Bacillus aneurinolyticus* (*Bacillus brevis*), Ionomycin calcium salt *Streptomyces conglobatus*, Lasalocid A sodium salt, Lonomycin A sodium salt from *Streptomyces ribosidificus*, Monensin sodium salt, N-(6-Aminohexyl)-5-chloro-1-naphthalenesulfonamide hydrochloride, Narasin from *Streptomyces auriofaciens*, Nigericin sodium salt from *Streptomyces hygroscopicus*, Nisin from *Streptococcus lactis*, Nonactin from *Streptomyces* sp., Nystatin, Nystatin powder, Phenazine methosulfate, Pimaricin, Pimaricin from *Streptomyces chattanoogensis*, Polymyxin B solution, Polymyxin B sulfate salt, DL-Penicillamine acetone adduct hydrochloride monohydrate, Polymyxin B sulfate salt powder USP, Praziquantel, Salinomycin from *Streptomyces albus*, Salinomycin from *Streptomyces albus*, Surfactin from *Bacillus subtilis*, Valinomycin, (+)-Usnic acid from *Usnea dasypoga*, (±)-Miconazole nitrate salt, (S)-(+)-Camptothecin, 1-Deoxymannojirimycin hydrochloride, 1-Deoxynojirimycin hydrochloride, 2-Heptyl-4-hydroxyquinoline N-oxide, Cordycepin, 1,10-Phenanthroline hydrochloride monohydrate puriss, 6-Diazo-5-oxo-L-norleucine, 8-Quinolinol crystalline, 8-Quinolinol hemisulfate salt, Antimycin A from *Streptomyces* sp., Antimycin $A_1$, Antimycin $A_2$, Antimycin A₃, Antipain, Ascomycin, Azaserine, Bafilomycin A1 from *Streptomyces griseus*, Bafilomycin B1 from *Streptomyces* species, Cerulenin BioChemika, Chloroquine diphosphate salt, Cinoxacin, Ciprofloxacin, Mevastatin BioChemika, Concanamycin A, Concanamycin A *Streptomyces* sp, Concanamycin C from *Streptomyces* species, Coumermycin A1, Cyclosporin A from *Tolypocladium inflatum*, Cyclosporin A, Econazole nitrate salt, Enrofloxacin, Etoposide, Flumequine, Formycin A, Furazolidone, Fusaric acid from *Gibberella fujikuroi*, Geldanamycin from *Streptomyces hygroscopicus*, Gliotoxin from *Gliocladium fimbriatum*, Gramicidin A from *Bacillus brevis*, Gramicidin C from *Bacillus brevis*, Gramicidin from *Bacillus aneurinolyticus* (*Bacillus brevis*), Gramicidin from *Bacillus brevis*, Herbimycin A from *Streptomyces hygroscopicus*, Indomethacin, Irgasan, Lomefloxacin hydrochloride, Mycophenolic acid powder, Myxothiazol BioChemika, N-(6-Aminohexyl)-5-chloro-1-naphthalenesulfonamide hydrochloride, Nalidixic acid, Netropsin dihydrochloride hydrate, Niclosamide, Nikkomycin BioChemika, Nikkomycin Z *Streptomyces tendae*, N-Methyl-1-deoxynojirimycin, Nogalamycin from *Streptomyces nogalater*, Nonactin □80% from *Streptomyces tsusimaensis*, Nonactin from *Streptomyces* sp., Novobiocin sodium salt, Ofloxacin, Oleandomycin triacetate, Oligomycin *Streptomyces diastatochromogenes*, Oligomycin A, Oligomycin B, Oligomycin C, Oligomycin *Streptomyces diastatochromogenes*, Oxolinic acid, Piericidin A from *Streptomyces mobaraensis*, Pipemidic acid, Radicicol from *Diheterospora chlamydosporia* solid, Rapamycin from *Streptomyces hygroscopicus*, Rebeccamycin from *Saccharothrix aerocolonigenes*, Sinefungin, Staurosporine *Streptomyces* sp., Stigmatellin, Succinylsulfathiazole, Sulfadiazine, Sulfadimethoxine, Sulfaguanidine purum, Sulfamethazine, Sulfamonomethoxine, Sulfanilamide, Sulfaquinoxaline sodium salt, Sulfasalazine, Sulfathiazole sodium salt, Triacsin C from *Streptomyces* sp., Trimethoprim, Trimethoprim lactate salt, Vineomycin A₁ from *Streptomyces albogriseolus* subsp., Tectorigenin, and Paracelsin *Trichoderma reesei*.

In a further embodiment the present invention relates to a kit of parts comprising the composition according to the present invention. The kit of parts comprises at least one additional component, such as instructions for use, and/or one or more drugs for co-administration.

EXPERIMENTAL

Example I

This example demonstrates that Nel dramatically reduces Ngo viability when the two species were cultured together in vitro (FIG. 1). Whether Nel inhibits Ngo growth in vitro was determined (FIG. 1).

Method: Nel 29315 $Sm^R$ and Ngo MS11 $Sm^R$ were suspended in liquid GCB+Supplements I/II, and inoculated together or alone into wells of tissue culture plates ($1 \times 10^7$ each species). The cultures were incubated at 37° C., 5% $CO_2$, and at various times triplicate wells were plated on GCB agar+Sm for Nel cfus, and GCB agar+VCN for Ngo cfus.

Result: Nel and Ngo grew normally when grown alone, but Ngo viability was reduced ~3 logs when Nel was present (5-hr vs 24-hr time point). Nel similarly reduced the viability of three fresh Ngo clinical isolates. Thus, Nel kills Ngo in liquid culture, and killing is not strain-specific.

Example II

This example demonstrates that Nel supernate reduces Ngo viability. It was determined whether the Nel compound that reduces Ngo viability is in the medium (FIG. 2).

Method: Nel was grown alone for 24 hrs in liquid GCB+Supplements I/II, at 37 C, 5% $CO_2$. Supernates were harvested at various times, filter sterilized, and incubated with Ngo MS11 for 5 hrs, in triplicate, and Ngo cfus were plated on GCB agar+VCN.

Result: Cell free supernates from the 12-hr and 18-hr time points reduced Ngo viability ~10-fold, while those from the 24-hr time point reduced viability >2.5 logs, compared to the 0-hr supernate (from Nel that had been freshly suspended in media). Three independent experiments yielded similar results. This suggests that Nel, in the absence of Ngo, releases/secretes a compound(s) into the medium that reduces Ngo viability.

Example III

This example shows that Nel DNA kills WT Ngo but not Ngo mutants that cannot take up or be transformed by neisserial DNA. In these experiments, $5 \times 10^5$ WT or mutant Ngo cells were incubated for 4 hours in presence or absence of Nel DNA (20 ug/mL). Ngo Only 22% of WT Ngo survived when cultured in the presence of Nel DNA (FIG. 3, first column) The Ngo ΔcomP mutant, which cannot bind to the neisserial DUS and therefore cannot take up neisserial DNA, is resistant to killing by Nel DNA (FIG. 3, second column) The complemented ΔcomP mutant, which expresses a WT copy of the comP gene, is now as sensitive to killing by Nel DNA as the WT Ngo strain (FIG. 3, third column) The Ngo ΔpilT mutant, which cannot take up the neisserial DNA that is bound to the ComP protein, is significantly more resistant to killing by Nel DNA, compared to WT Ngo (FIG. 3, fourth column) The Ngo N400 mutant, which cannot be transformed by DNA because it cannot recombine the entering DNA into its genome, is as resistant to killing by Nel DNA as the ΔcomP mutant (FIG. 3, fifth column) Taken together, these results indicate that the sensitivity of Ngo to killing by Nel requires its ability to take up neisserial DNA, and that the killing activity of Nel consists at least in part to its DNA.

Example IV

This example demonstrates Nel killing of Ngo is replicated by an agar plate assay. An agar plate assay was developed to study Ngo killing by Nel supernate (FIG. 4).

Method: An agar plate assay was developed to detect killing of Ngo by Nel supernate Ngo (see, FIG. 4). Ngo MS11 cells are spread evenly (uniformly distributed) over an agar plate. Different concentrations (same volume) of highly purified (protein and RNA free) Npo DNA are spotted onto the lawn of Ngo cells, and the plate is incubated overnight at 37° C. After overnight incubation, Ngo cells will grow into a dense and opaque lawn that is visible by eye. A clear zone in the lawn where a DNA solution was applied indicates that that DNA has killed Ngo cells. The negative control for this assay is GC buffer. The positive control for this assay is Kanamycin (Kan) (50 mg/uL).

Result: The 24-hr cell free Nel supernate and Kanamycin (50 ug/ml) produced clear zones on the lawn, indicating they inhibited Ngo growth, while GC buffer did not affect Ngo growth.

Example V

This example demonstrates that Ngo susceptibility to killing involves its uptake of Nel DNA. The nature of the lethal compound in the Nel supernate was determined using the agar plate assay.

Experimental protocol: Nel cells were grown in liquid for 24 hours, and the cells were pelleted by centrifugation. The supernate was passed through a membrane with small pores to remove any remaining bacteria. A portion of the filtered supernate was plated on agar to corroborate its sterility. The sterile 24-hr Nel supernate was subjected to various treatments and these samples were assessed for their ability to kill Ngo using the agar plate assay.

Result: Boiling, digestion with RNAse-free DNAse I, and UV cross-linking abolished the ability of the Nel supernate to kill Ngo. Proteinase K digestion and RNAse A digestion did not affect its killing activity. This suggests that Nel supernate killing of Ngo involves a DNA component (Table 1).

TABLE 1

Anti-Ngo activity of Nel supernates and DNAs; and susceptibility of Ngo mutants to killing by 24-hr Nel supernate. (+) Killing; (−) No killing.

| | Exp1 | Exp2 | Exp3 |
|---|---|---|---|
| Treatment of supernate | | | |
| 37 C., 3 hr | + | + | + |
| 100 C., 3 hr | − | − | − |
| DNAse I | − | − | − |
| Boiled DNAse I (100 C., 3 hr) | + | + | + |
| UV, 30 min | − | − | − |
| Mock UV, 30 min | + | + | + |
| Proteinase K | + | + | + |
| Proteinas K (boiled 1 hr) | + | + | + |
| DNA | | | |
| Nel DNA | + | + | + |
| Ngo DNA | − | − | − |
| Nme DNA | − | − | − |
| E. Coli DNA | − | − | − |
| Nel DNA + DNAse I | − | − | − |
| Nel DNA + HpyCH4IV | − | − | − |
| Nel DNA + HpyCH4IV buffer | + | + | + |
| Nel DNA + SfoI | − | − | − |
| Nel DNA + SfoI buffer | + | + | + |
| Nel DNA + BglII | + | + | + |
| Nel DNA + BglII buffer | + | + | + |
| Ngo strains | | | |
| MS11 wt | + | + | + |
| MS11ΔpilT | − | − | − |
| MS11ΔpilE | − | − | − |
| MS11ΔcomP | − | − | − |

Nel does not have plasmids (see, e.g., Swanson, J., J Exp Med, 1973. 137(3): p. 571-89). It was determined whether Nel chromosomal DNA kills Ngo. Method: chromosomal DNA from Nel, Ngo, Nme and E. coli was digested with RNAse A, extracted with phenol/chloroform/isopropanol, and washed twice with ethanol. All DNAs have an $OD_{260/280}$ ratio of ≥1.98 (highly pure). The DNAs were spotted (30 ng/uL) on a Ngo lawn to test killing activity.

Result: Only purified Nel DNA killed Ngo (Table 1). The purity of the DNA argues against the Trojan Horse theory, whereby an agent enters Ngo by "hitchhiking" on Nel DNA. Ngo, Nme and E. coli DNA did not kill Nel.

Neisseria are naturally competent and readily take up DNA. DNA uptake requires retraction of the Type IV pilus (Tfp) fiber and binding of ComP, a pilus-associated protein, to a 10-bp DNA uptake sequence (DUS) that is abundant in neisserial genomes (see, e.g., Swanson, J., J Exp Med, 1973. 137(3): p. 571-89; Wolfgang, M., et al., Mol Microbiol, 1999. 31(5): p. 1345-57; Berry, J. L., et al., PLoS Genet, 2013. 9(12): p. e1004014). Mutations in pilE, the Tfp fiber subunit gene (see, e.g., Merz, A. J., M. So, and M. P. Sheetz, Nature, 2000. 407(6800): p. 98-102); pilT, the Tfp retraction motor gene (see, e.g., Merz, A. J., M. So, and M. P. Sheetz, Nature, 2000. 407(6800): p. 98-102); and comP (see, e.g., Berry, J. L., et al., PLoS Genet, 2013. 9(12): p. e1004014; Cehovin, A., et al., Proc Natl Acad Sci USA, 2013. 110(8): p. 3065-70) abolish competence.

It was determined whether DNA uptake by Ngo is required for its susceptibility to killing by Nel supernate.

Method 1: Wt Ngo MS11, MS11ΔpilE, MS11ΔpilT and MS11ΔcomP were tested for susceptibility to killing by 24-hr cell free Nel supernates, using the agar plate assay. In MS11ΔcomP, a Kanamycin (Kan) resistance cassette has replaced comP; this in-frame mutation does not affect expression of flanking genes. Result: All mutants were resistant to supernate killing, unlike the wt strain (Table 1). Thus, DNA uptake by Ngo via Tfp/DUS is key to its susceptibility to killing by Nel supernate.

Method 2: Nel DNA was digested with restriction enzymes HpyCH4IV (which cuts in the DNA uptake sequence (DUS)), SfoI, or BglII, or incubated with buffer alone, and the samples were tested for killing activity using the plate assay. Result: HpyCH4IV and SfoI, but not BglII or any of the buffers, abolished killing activity (Table 1). The HpyCH4IV result strongly suggests that the lethal effect of Nel DNA on Ngo requires intact DUSs. The SfoI result suggests that at least one other enzyme abolishes the ability of Nel DNA to kill Ngo.

Example VI

This example demonstrates DNAse I prevents Nel killing of Ngo in liquid culture. It was determined whether DNAse I could protect Ngo from Nel killing in liquid culture.

Method: Nel and Ngo were preincubated separately with DNAse I (50 U/mL) or buffer for 30 min, then either mixed together or kept in separate tubes, and incubated for 5 hrs. DNAse I (50 U/mL) or buffer was added twice more to the tubes, at 2 and 4 hrs. Nel and Ngo cfus from three independent experiments were averaged and the median values compared using Students' t-test.

Result: In the mixed cultures, DNAse I increased Ngo viability ~20-fold over the buffer control (p<0.001). DNase I did not affect Nel cfus in the mixed cultures, or Nel or Ngo cfus in the monocultures. This firmly supports the agar plate assay findings, indicating Nel DNA is the agent that kills Ngo in liquid culture.

Example VII

This example demonstrates that Nel dramatically reduces Ngo cfus in the lower genital tract of mice and accelerates its clearance. Ngo does not cause disease in animals. A mouse model for studying Ngo colonization and adaptation in the female lower genital tract has been developed (see, e.g., Jerse, A. E., et al., Front Microbiol, 2011.2: p. 107). In this system, Ngo persists in the mouse vagina for 10-12 days before it is cleared by the innate defense system. This model recapitulates many events in Ngo infection in humans: 1) cytokine/chemokine production, PMN recruitment, an unprotective antibody response, and induction/suppression of Th17/Th1/Th2 responses (see, e.g., Packiam, M., et al., Mucosal Immunol, 2012. 5(1): p. 19-29; Wu, H., A. A. Soler-Garcia, and A. E. Jerse, Infect Immun, 2009. 77(3): p. 1091-102); 2) human innate defenses (see, e.g., Packiam, M., et al., Mucosal Immunol, 2012. 5(1): p. 19-29; Wu, H., A. A. Soler-Garcia, and A. E. Jerse, Infect Immun, 2009.

77(3): p. 1091-102); and 3) Opa antigenic variation (see, e.g., Simms, A. N. and A. E. Jerse, Infect Immun, 2006. 74(5): p. 2965-74; Cole, J. G., N. B. Fulcher, and A. E. Jerse, Infect Immun, 2010. 78(4): p. 1629-41). Jerse's model is used to test the role of Ngo factors in protecting against host innate defenses (see, e.g., Wu, H., A. A. Soler-Garcia, and A. E. Jerse, Infect Immun, 2009. 77(3): p. 1091-102; Warner, D. M., et al., J Infect Dis, 2007. 196(12): p. 1804-12; Warner, D. M., W. M. Shafer, and A. E. Jerse, Mol Microbiol, 2008. 70(2): p. 462-78).

Whether commensal *Neisseria* antagonizes Ngo was determined using this mouse model. Nel strain 29315 was focused on because its genome is sequenced (see, e.g., Marri, P. R., et al., PLoS One, 2010. 5(7): p. e11835) and Ngo strain MS11 (see, e.g., Swanson, J., J Exp Med, 1973. 137(3): p. 571-89) because its host cell interactions are well studied. Both strains are resistant to Streptomycin ($Sm^R$) to allow colonization of Sm-treated mice, and both grow as well as their wt parents.

Method: Mice were inoculated in the vagina with Nel or Ngo alone, or Nel+Ngo. The vaginas were swabbed periodically and swab suspensions were plated on L agar+Sm for Nel colony forming units (cfus), and GCB agar+Vancomycin, Colistin, and Nalidixic Acid (VCN) for Ngo cfus.

Figure 5A:
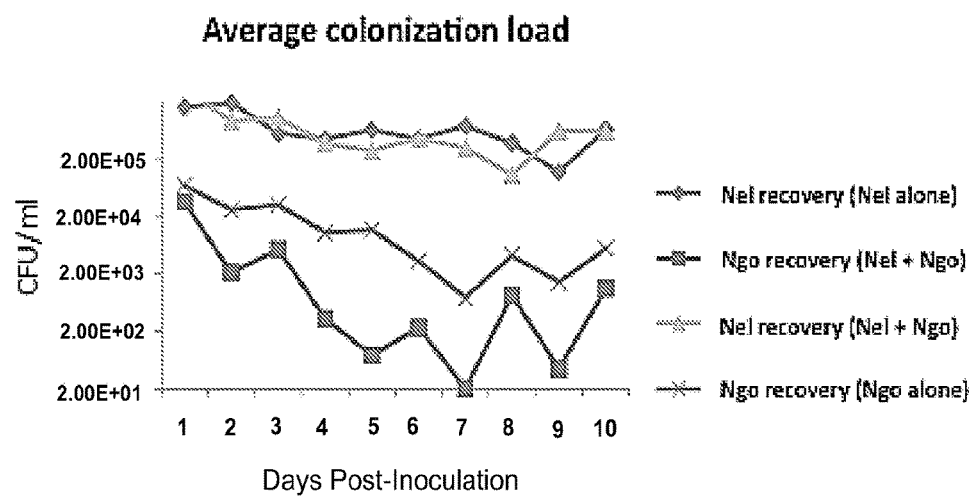
FIG. 5A and FIG. 5B: Ngo is cleared from mice more quickly when in the presence of Nel. The vagina of mice were inoculated with Ngo alone, or with a 50:50 ratio of Ngo and Nel and Ngo counts were measured over the course of 10 days.
Figure 5B:
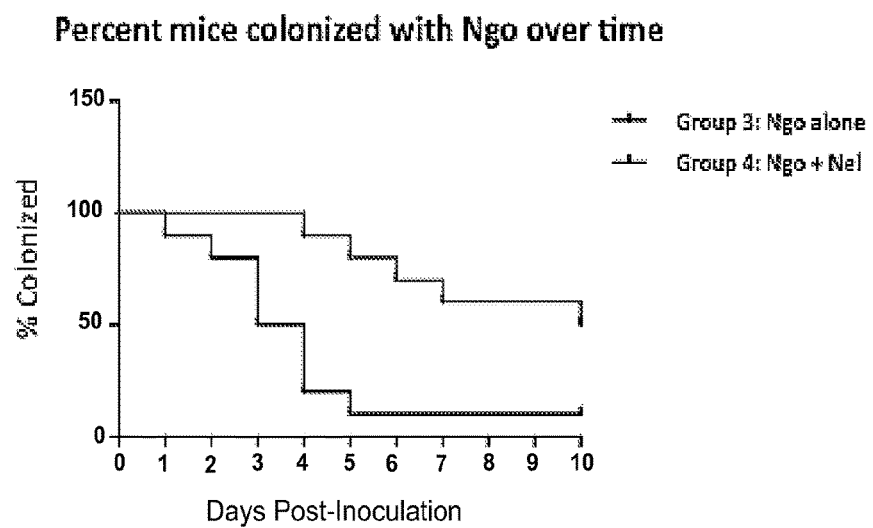
Figure 6A:
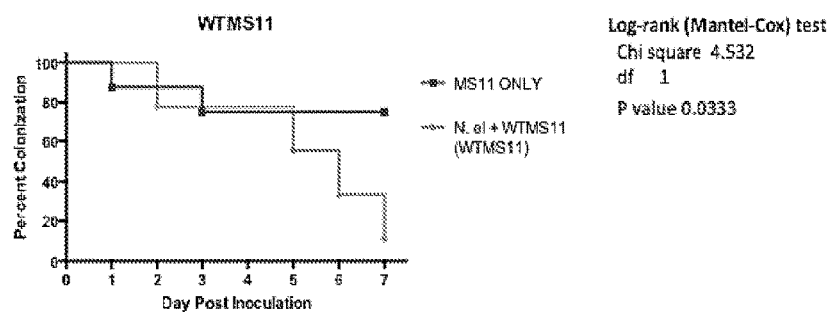
FIG. 6A and FIG. 6B: The DNA uptake mutant, Ngo DcomP, is resistant to Nel clearance from mice, compared to WT Ngo.
Figure 6B:
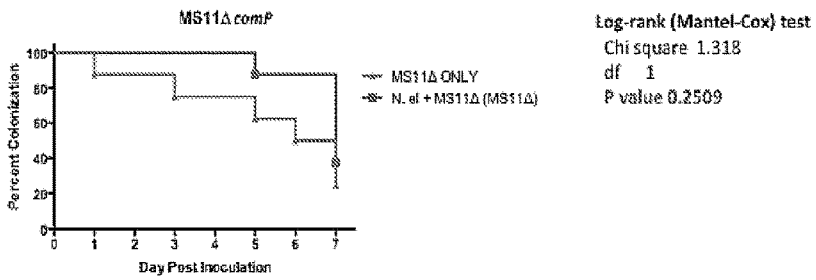

Result: Ngo was recovered at significantly lower levels from mice co-infected with Nel than mice inoculated with Ngo alone (FIG. 5A, red vs purple line). In addition, the duration of Ngo infection was significantly shorter in co-infected mice than mice infected with Ngo alone (3 days vs 7.7 days; FIG. 5B, blue vs red line). In co-infected mice, Ngo was cleared from 50% of the animals by day 3, and from 90% of the animals by day 5. In mice infected with Ngo alone, Ngo was recovered from 100% of the animals on day 3, and from 80% of the animals on day 5. In contrast, Nel was recovered from mice at high levels throughout the 10-day period whether Ngo was present or not (range of average cfu/ml: $1 \times 10^5$ to $3 \times 10^6$) (FIG. 5A). These results suggest that Ngo MS11 was cleared more quickly from mice when Nel was present.

That Nel colonizes the lower genital tract of female mice is a novel finding. It suggests the potential of this model for studying commensal *Neisseria* colonization, persistence and interactions with pathogens.

Example VIII

This example involves identification of the Nel locus/loci lethal for Ngo.

SmR strains of Nel 29315 (see, e.g., Swanson, J., J Exp Med, 1973. 137(3): p. 571-89) and Ngo MS11 (see, e.g., Swanson, J., J Exp Med, 1973. 137(3): p. 571-89) or their derivatives will be used in additional experiments. Both genomes are sequenced; both are piliated; Nel 29315 does not have opa genes; Ngo MS11 does not express Opa. Bacteria will be cultured in GCB medium+Supplements I/II or GCB agar.

Methods to identify the *N. elongata* locus/loci that kills Ngo have been identified. It involves identifying restriction enzymes that cut in the sequences crucial for killing Ngo, and matching the enzyme recognition sites to the restriction map of the *N. elongata* genome. Proof of principle for this method comes from the observations that Nel DNA kills Ngo when it is taken up by the pathogen, and its ability to kill is destroyed when it is digested with a restriction enzyme that cuts in the DUS.

Using the 2.26 Mb Nel 29315 genome sequence (see, e.g., Swanson, J., J Exp Med, 1973. 137(3): p. 571-89) as the starting point, restriction maps of the 53 contigs (the genome is not closed) will be constructed, using programs on the web. Nel DNA will be digested with 50 separate restriction enzymes (more if necessary), and the samples tested for Ngo killing activity using the agar plate assay. Enzyme selection will be guided by the restriction maps and by enzyme requirements.

Nel DNA will be extracted as described in Example V. DNA with $OD_{260/280}$ ratios ≥1.98 will be digested with enzymes per manufacturers' instructions, and spotted (30 ng/uL) on a lawn of Ngo MS11 to test for killing activity. Digestion will be monitored by agarose gel electrophoresis. Controls are: Nel DNA spiked with a plasmid containing a site for the enzyme to monitor digestion; Nel DNA incubated with buffer alone; enzyme alone; and *E. coli* DNA incubated with enzyme or buffer alone (*E. coli* DNA does not kill Ngo; Table 1). Three independent experiments will be performed.

DNAs allowing Ngo growth will be assigned a value of 1; enzymes in these samples are presumed to cut in the lethal locus or sequences important for its expression. DNAs that kill Ngo will be assigned a value of 0; enzymes in these samples are presumed not to interrupt these sequences. Scores for each enzyme will be tallied for all three experiments. A few enzymes will have a score of 3; most will have a score of 0. Enzymes with intermediate scores (e.g., score of 2; values of 1, 1, 0) will be retested, as the reactions may not have gone to completion. Enzymes and scores will be matched to the restriction map of each contig (FIG. 8).

A region with a cluster of high scoring enzymes and devoid of low scoring enzymes is presumed to contain a locus deleterious to Ngo. If the region is still very large, with many open reading frames, we will map it with additional enzymes, choosing ones that are in the restriction map of the contig. The region will be analyzed for determinants of cell death-inducing systems as discussed above and (see, e.g., Cascales, E., et al., Microbiol Mol Biol Rev, 2007. 71(1): p. 158-229; Makarova, K. S., Y. I. Wolf, and E. V. Koonin, Nucleic Acids Res, 2013. 41(8): p. 4360-77), and DUS. It is anticipated that one locus will be identified, two or more distinct loci, or multiple copies of the same locus, and a DUS within 1-2 kb of the locus/loci because of its abundance in neisserial genomes (see, e.g., Swanson, J., J Exp Med, 1973. 137(3): p. 571-89).

Experiments will be conducted to validate the results from above. The presumptively positive region(s) will be PCR amplified with flanking primers and directly assess the DNA for killing activity using the plate assay. PCR does not work well for very large regions of DNA; if faced with this situation, the presumptive positive region(s) will be cloned into a plasmid in *E. coli* and test the plasmid DNA for killing activity using the plate assay. The control is empty plasmid DNA. Subsequent subcloning and testing will pinpoint the sequences important for lethality.

A Nel mutant will be constructed that is deleted of the locus and complement the mutant, using standard protocols for *Neisseria* (see, e.g., Dillard, J. P., Curr Protoc in Microbiol, 2011 (Chapter 4:Unit4A.2)). Mutants have been successfully made in Nel. If multiple loci are identified, a mutant will be constructed with multiple deletions and a corresponding complemented strain. DNA from the mutant (s) and complemented mutant(s) will be tested for killing activity using the plate assay. The strains will also be co-cultured with Ngo (see Example II) to test their ability to kill the pathogen. The strains will be tested in mice, as described in (see, e.g., Jerse, A. E., et al., Front Microbiol, 2011. 2: p. 107) and below.

Large fragments of Nel DNA will be cloned into a plasmid vector in E. coli, and test plasmid DNAs for killing activity using the plate assay. Large fragments of Nel DNA will be generated by digestion with an enzyme with few sites in the Nel genome and which leaves the lethal locus intact (determined by the plate assay). Subsequent subcloning will pinpoint the locus/loci. Fragments will be inserted into a vector which accommodates large inserts, such as BAC (Bacterial Artificial Chromosome).

Example IX

This example involves determining whether Ngo DNA uptake mutants resist Nel clearing from mice.

The mouse model of Ngo genital tract infection was used to test whether uptake of Nel DNA by Ngo is the mechanism by which it is cleared in vivo. MS11 comP was examined in particular. This mutant cannot bind to the neisserial DUS and therefore cannot take up neisserial DNA, but it behaves normally in Tfp biogenesis, twitching motility and infection of cultured cells (see, e.g., Wolfgang, M., et al., Mol Microbiol, 1999. 31(5): p. 1345-57; Berry, J. L., et al., PLoS Genet, 2013. 9(12): p. e1004014). MS11ΔpilE or MS11ΔpilT were not tested in mice as in vitro studies show MS11ΔpilE does not attach to cells, and MS11ΔpilT signals epithelial cells aberrantly, with consequences for later stages of infection (see, e.g., Merz, A. J. and M. So, Annu Rev Cell Dev Biol, 2000. 16: p. 423-57; Howie, H. L., S. L. Shiflett, and M. So, Infect Immun, 2008. 76(6): p. 2715-21). Neither ΔpilE nor ΔpilT has been tested in mice.

BALB/c mice (4-6 weeks old) were treated with 17β-estradiol and Streptomycin (Sm) using a standard protocol (Jerse, A. E., et al., Front Microbiol, 2011. 2: p. 107). Three groups of mice (8/group) were inoculated vaginally with a suspension containing similar numbers of Nel and either WT MS11, MS11 compP, or the complemented mutant MS11ΔcomP+comP$_{wt}$. Control mice were inoculated with each strain alone. Vaginal swabs were collected daily for the duration of the experiment, and bacterial counts in swab suspensions were determined by plating on GC agar+Sm for Ng colony forming units (cfus), and Heart Infusion Agar (HIA) for Nel cfus. The duration of colonization of test and control groups were plotted as Kaplan Meier colonization curves and analyzed using the LogRank test. The cfus recovered over time in test and control groups were compared using a repeated measures ANOVA followed by a Bonferroni post-hoc analysis. For both sets of analyses, $p<0.05$ were considered significant. Experiments were performed at least twice to increase statistical power and test data reproducibility.

These experiments (see FIG. 5A-B, FIG. 6A-B, and FIG. 7A B) show that WT MS11 colonized mice for a shorter period of time when Nel is present than when Nel is absent. ΔcomP persisted in mice for a longer period than WT MS11 whether Nel is present or not. MS11ΔcomP+comP$_{wt}$, the complemented mutant, behaved like the Wt strain, i.e., it colonized mice for a shorter period of time than the ΔcomP mutant.

The complemented mutant MS11ΔcomP+comP$_{wt}$ was constructed using standard Neisseria mutagenesis protocols (see, e.g., Dillard, J. P., Curr Protoc in Microbiol, 2011 (Chapter 4:Unit4A.2); Ramsey, M. E., et al., Appl Environ Microbiol, 2012. 78(9): p. 3068-78). The wt comP gene with an Erythromycin (Erm) cassette and a DUS downstream were introduced into an intergenic region of wt MS11 described previously (see, e.g., Dillard, J. P., Curr Protoc in Microbiol, 2011 (Chapter 4:Unit4A.2)). This construct also contained comP promoter elements. ΔcomP::Kan DNA was then transformed into this strain. The two loci were sequenced. All strains (wt MS11, MS11ΔcomP, and MS11ΔcomP+comP$_{wt}$) were tested for their ability to take up DNA and their growth curves examined.

Example X

This example demonstrated that Npo DNA kills Ngo. It was determined whether Npo DNA kills Ngo using the agar plate assay.

Positive control: Nel DNA, Kanamycin (Kan; 50 mg/uL)
Negative control: fresh sterile medium (GC medium)
NG=No growth; G=growth; SN=fresh undiluted Nel supernatant
Prep #=Nel supernate preparations with proven killing activity against Ngo MS11
Spot ID=position of spot on plate
Photo ID #=image of a plate or position of a plate containing the result in question I

| Spot ID | Sample | Concentration (ng/uL) | Photo ID # | Growth/No Growth | Photo ID # | Growth/No Growth |
|---|---|---|---|---|---|---|
| 1 | DNA Nel prep #7 | 60 | 100-6817 | NG | 100-6852 | NG |
| 2 | | 30 | 100-6816 | NG | 51 | NG |
| 3 | | 15 | 15 | NG | 50 | NG |
| 4 | | 7.5 | 14 | NG | 49 | NG |
| 5 | DNA Nel prep #10 | 60 | 24 | NG | 53 | NG |
| 6 | | 30 | 23 | NG | 54 | NG |
| 7 | | 15 | 22 | NG | 55 | NG |
| 8 | | 7.5 | 21 | NG | 56 | NG |
| 9 | DNA Npo | 60 | 41 | +/− | 57 | NG |
| 10 | | 30 | 40 | NG | 58 | NG |
| 11 | | 15 | 39 | NG | | NG |
| 12 | | 7.5 | 38 | NG | | +/− |
| C+ | Kanamycin | 5 mg/mL | 48 | NG | | NG |
| C− | GC medium | | 47 | G | | G |
| C+ | SN | | 46 | NG | | NG |

II

| Spot ID | Sample | Concentration (ng/uL) | Photo ID # | Growth/No Growth |
|---|---|---|---|---|
| 1 | DNA Nel prep #7 | — | | |
| 2 | | 3.75 | [100-]6819 | G |
| 3 | | 1.875 | 18 | G |
| 4 | | 0.9375 | 20 | G |
| 5 | DNA Nel prep #10 | 3.75 | 25 | G |
| 6 | | 1.875 | 26 | G |
| 7 | | 0.9375 | 6827 | G |
| 8 | | — | | G |
| 9 | DNA N poly | 3.75 | [68]32/[68]42 | G |
| 10 | | 1.875 | 6833/[68]43 | G |
| 11 | | 0.9375 | [100-68]44 | G |
| 12 | | — | | |
| C+ | Kanamycin (5 mg/mL) | | | NG |
| C- | GC medium | | | G |
| C+ | SN | | [100-68]45 | NG |

Example XI

This example investigates whether a gene transfer between *N. elongata* and *N. gonorrhoeae* is responsible for Ngo inhibition during coinfection. In particular, Ngo inhibition was compared between a *N. gonorrhoeae* ΔcomP mutant that is unable to take up DNA compared and the wild type strain. Five groups of eight mice were tested in the following manner:

Group 1: *N. elongata* alone ($10^6$ CFU)
Group 2: Ngo strain MS11 Wild Type alone ($10^6$ CFU)
Group 3: Ngo strain MS11ΔcomP (mutant) alone ($10^6$ CFU)
Group 4: *N. elongata*+Ngo strain MS11 Wild Type ($10^6$ CFU)
Group 5: *N. elongata*+Ngo strain MS11Δ comP ($10^6$ CFU)

Group 1, 2, & 4 inocula were prepared together for the *N. elongata* solo group, MS11 wild type solo group, and *N. elongata*+MS11 wild group. Group 3 & 5 inocula were prepared about 45 min later with a new batch of *N. elongata* for experiments with the MS114 comP only and *N. elongata*+MS11ΔcomP groups.

Figure 7A:
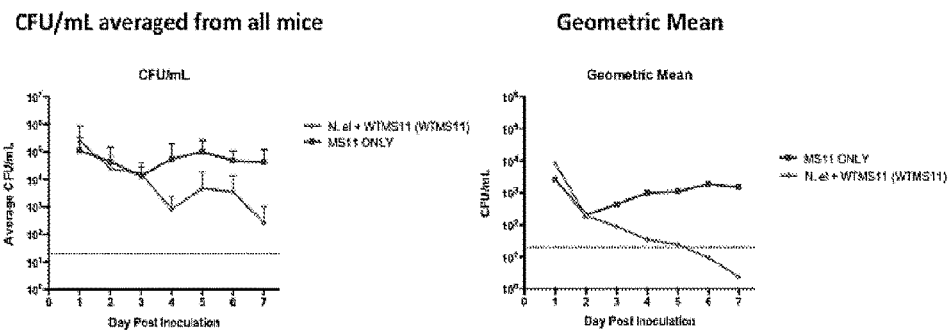
Figure 7B:
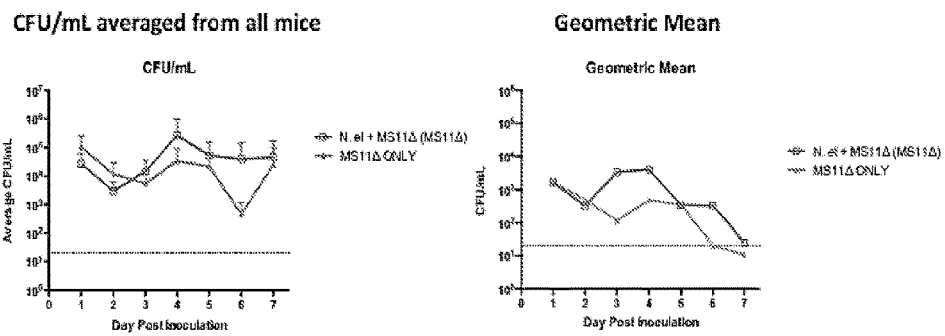

It was found that the MS11ΔcomP mutant is able to survive during coinfection with N *elongata*, but the wild type parent strain of Ngo is cleared at a significant rate when coinfected with *N. elongata* in vivo compared to infections with the wild type parent alone (see, FIGS. 5, 6 and 7). These results are consistent with the hypothesis that a DNA transfer from *N. elongata* to *N. gonorrhoeae* is responsible for *N. elongata*-mediated inhibition of Ngo in vivo.

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

INCORPORATION BY REFERENCE

The entire disclosure of each of the patent documents and scientific articles referred to herein is incorporated by reference for all purposes. The following references are referenced within this application and are herein incorporated by reference in all entireties:

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

We claim:

1. A method for the inhibition of *Neisseria gonorrhoeae* (Ngo) growth and/or for the killing of Ngo in a product, said method comprising the step of adding to the Ngo a composition comprising an effective amount of a purified genomic DNA of a commensal species of *Neisseria* selected from the group consisting of *Neisseria elongata* (Nel) and *Neisseria polysaccharea* (Npo), wherein the uptake of the genomic DNA by the Ngo inhibits the growth of said Ngo and/or kills said Ngo.

2. The method of claim 1, wherein said composition is an antibacterial composition selected from the group consisting of a preservative, an antiseptic, a disinfectant, an antifouling agent, and a medicament.

3. The method of claim 2, wherein said antibacterial composition is a preservative in a food product, a feed composition, a beverage, a cosmetic or a pharmaceutical composition.

* * * * *